(12) United States Patent
Dimarco

(10) Patent No.: US 10,549,100 B2
(45) Date of Patent: Feb. 4, 2020

(54) SYSTEM AND METHOD FOR ACTIVATING INSPIRATORY AND EXPIRATORY MUSCLE FUNCTION

(71) Applicant: Anthony F. Dimarco, Solon, OH (US)

(72) Inventor: Anthony F. Dimarco, Solon, OH (US)

(*) Notice: Subject to any disclaimer, the term of this patent is extended or adjusted under 35 U.S.C. 154(b) by 192 days.

(21) Appl. No.: 15/644,006

(22) Filed: Jul. 7, 2017

(65) Prior Publication Data
US 2018/0008826 A1    Jan. 11, 2018

Related U.S. Application Data

(60) Provisional application No. 62/360,098, filed on Jul. 8, 2016.

(51) Int. Cl.
| A61N 1/36 | (2006.01) |
| A61N 1/05 | (2006.01) |
| A61N 1/06 | (2006.01) |

(52) U.S. Cl.
CPC .......... *A61N 1/3611* (2013.01); *A61N 1/0551* (2013.01); *A61N 1/36171* (2013.01); *A61N 1/06* (2013.01); *A61N 1/36003* (2013.01)

(58) Field of Classification Search
CPC ... A61N 1/3611; A61N 1/0551; A61N 1/3601
See application file for complete search history.

(56) References Cited

U.S. PATENT DOCUMENTS

| 4,830,008 | A | 5/1989 | Meer |
| 5,058,584 | A | 10/1991 | Bourgeois |
| 5,524,632 | A | 6/1996 | Stein et al. |
| 5,540,732 | A | 7/1996 | Testerman |
| 5,678,535 | A | 10/1997 | Dimarco |
| 5,911,218 | A | 6/1999 | Dimarco |
| 5,999,855 | A | 12/1999 | Dimarco |
| 6,233,488 | B1 | 5/2001 | Hess |
| 7,047,079 | B2 | 5/2006 | Erickson |
| 7,840,270 | B2 | 11/2010 | Ignagni et al. |
| 8,352,036 | B2 | 1/2013 | Dimarco et al. |
| 2002/0188332 | A1 | 12/2002 | Lurie et al. |
| 2004/0088015 | A1 | 5/2004 | Casavant et al. |
| 2008/0051851 | A1 | 2/2008 | Lin |

(Continued)

OTHER PUBLICATIONS

Dimarco, et al., "Effects of Diaphragm Activation on Airway Pressure Generation During Lower Thoracic Spinal Cord Stimulation", Respiratory Physiology & Neurobiology, 2007, pp. 102-107, vol. 190, Elsevier.

(Continued)

*Primary Examiner* — Tammie K Marlen
(74) *Attorney, Agent, or Firm* — Curatolo Sidoti Co., LPA; Salvatore A. Sidoti

(57) ABSTRACT

A system and method for restoring inspiratory muscle function to restore breathing and expiratory muscle function to restore an effective cough in the same individual, wherein the systems that selectively activate the inspiratory or expiratory muscle function are separately ground to limit or prevent the flow of electrical current to both the expiratory and inspiratory muscles at the same time and to avoid damaging either neuromuscular system. Also described is the method by which the inspiratory or expiratory muscles are activated selectively to optimize the action of the inspiratory muscles to restore breathing and to optimize the action of the expiratory muscles to restore cough.

31 Claims, 8 Drawing Sheets

(56) References Cited

U.S. PATENT DOCUMENTS

2010/0185253 A1    7/2010   Dimarco et al.
2013/0289636 A1   10/2013   Karamanoglu et al.
2014/0058490 A1    2/2014   Dimarco

OTHER PUBLICATIONS

Brown, et al., "Respiratory Dysfunction and Management in Spinal Cord Injury", The Science Journal of the American Association for Respiratory Care, Aug. 2006, pp. 853-870, vol. 51, Issue No. 8, Irving, TX.

Butler, J.E., et al., "Discharge Properties and Recruitment of Human Diaphragmatic Motor Units During Voluntary Inspiratory Tasks", Journal of Physiology; pp. 907-920, 1999.

Gandevia, et al., "Spatial Distribution of Inspiratory Drive to the Parasternal Intercostal Muscles in Humans", The Physiological Society, 2006, pp. 263-275.

Detroyer, et al., "Distribution of Inspiratory Drive to the External Intercostal Muscles in Humans"; The Physiological Society, 2002, pp. 943-954.

Gandevia, et al, "Effects of Increased Ventilatory Drive on Motor Unit Filing Rates in Human Inspiratory Muscles", American Journal of Respiratory and Critical Care Medicine of the American Thoracic Society, Apr. 5, 1999, pp. 1598-1603, vol. 160, NewYork.

PCT/US2017/041145—International Search Report, dated Sep. 13, 2017.

EXTERNAL COMPONENTS

INTERNAL COMPONENTS

… … …

SYSTEM AND METHOD FOR ACTIVATING INSPIRATORY AND EXPIRATORY MUSCLE FUNCTION

This application claims the benefit of the filing date under 35 U.S.C. § 119(e) of United States Provisional Application For Patent Ser. No. 62/360,098 filed on Jul. 8, 2016, which is incorporated herein by reference.

TECHNICAL FIELD

Patients with high level cervical tetraplegia are unable to breathe spontaneously and are dependent upon mechanical ventilation due to paralysis of their inspiratory muscles. In addition, these patients cannot cough to clear their airways due to paralysis of their expiratory muscles. Disclosed is a system and method for restoring both inspiratory and expiratory muscle function in the same individual. More specifically, the system and method is directed to selectively restoring inspiratory muscle function by applying electrical stimulation to the phrenic nerves and/or upper thoracic spinal cord and restoring expiratory muscle function by applying electrical stimulation to the lower thoracic spinal cord and/or the upper lumbar spinal cord.

BACKGROUND

Normal respiration involves the act of breathing, i.e., inhaling (inspiration) and exhaling (expiration). It is by the act of breathing that the lungs are supplied with oxygen and carbon dioxide is removed during exhalation.

During inspiration, air is inhaled into the lungs and is transferred to the blood by the gaseous exchange that occurs by the capillaries in the walls in the pulmonary alveoli. The oxygen present in the blood is utilized by the tissues resulting in the production of carbon dioxide. The carbon dioxide is in turn removed from the blood by a similar gaseous exchange that occurs at the pulmonary alveoli. During expiration, the carbon dioxide and other related pulmonary gases are removed from the body.

During normal breathing, the chest wall and abdomen both expand during inspiration and retract during expiration. At rest, inspiration lasts for about one second and expiration lasts for about four seconds. Contraction of the inspiratory muscles reduces intrapleural pressure thereby expanding the lungs and drawing air into the respiratory passages. The expiratory phase is largely passive, wherein recoil of the thoracic wall and lungs raises intrathoracic pressure to expel air.

The expansion of the thoracic cavity during inspiration is brought about by contraction of the diaphragm and intercostal muscles. The diaphragm is a modified half-dome of musculofibrous tissues separating the thorax and abdomen. The diaphragm is the chief muscle of respiration. The intercostal muscles are the inner and outer layer of muscles between the ribs. The inner layer has an expiratory function to cause exhalation while the outer layer has an inspiratory function to cause inhalation.

The muscle movements related to inspiration are generally controlled by the phrenic and intercostal nerves. The diaphragm is innervated by the left and right phrenic nerves. Spinal cord injury at the cervical and/or thoracic level can cause disruption of nerve impulses that travel from the brain to the phrenic and intercostal nerves, resulting in paralysis of the diaphragm and intercostal muscles necessitating the use of a lung assist device, such as a ventilator.

Previously, in patients suffering from respiratory muscle paralysis due to injury of the cervical spinal cord, various attempts have been made to produce artificial respiration by electrical stimulation of the phrenic nerves. In this regard, diaphragm pacing has been used successfully to restore ventilation resulting in liberation of patients from mechanical ventilation. Previous attempts have also been made to restore an effective cough by electrical stimulation techniques. For example, lower thoracic spinal cord stimulation has been successful in causing activation of the expiratory muscles and restoration of an effective cough.

Normal cough is a reflex following inspiration which includes in order: glottic closure, contraction of the expiratory muscles, and opening of the glottis. To accomplish this cycle in a patient with a diaphragm pacing system in place requires precise timing of the inspiration by the pacing system and airway occlusion at the peak of inspiration to generate the most effective cough. Further, if there is not a full inspiration to sufficiently stretch the expiratory muscles, the cough will be much less effective and will not adequately remove airway secretions or aspirated material such as food or other foreign bodies from the airway.

BRIEF DESCRIPTION

Disclosed is a system and method for selectively activating both the inspiratory and expiratory muscles to restore both breathing and coughing in the same subject. More particularly, the system and method is directed to inspiratory and expiratory electrical stimulation systems that are capable of controlling the delivery of an electrical stimulation to the inspiratory and expiratory muscle motor neurons in a subject. The term "subject", as used herein, refers to a human or non-human animal, such as a domesticated farm animal (e.g., cow, horse, pig) or pet (e.g., dog, cat, etc.).

In some embodiments, the method for producing coordinated contraction and relaxation of the respiratory muscles in a subject comprises:

positioning one or more first electrical stimulators on one or both phrenic nerves in the cervical region, in the thorax, within the muscular body of the diaphragm near the motor point of the phrenic nerve, at one or more levels of the upper thoracic spinal cord, or combinations thereof of the subject;

positioning one or more second electrical stimulators at one or more levels of the lower thoracic spinal cord, upper lumbar spinal cord, or combinations thereof of the subject;

selectively operating the one or more first and second electrical stimulators to deliver an electrical stimulation to activate the inspiratory or expiratory muscles;

wherein activation of the one or more first electrical stimulators activates the inspiratory muscles to restore breathing and activation of the one or more second electrical stimulators provides coordinated contraction of the expiratory muscles to restore an effective cough; and wherein the one or more first electrical stimulators and one or more second electrical stimulators are separately ground to limit or prevent the flow of electrical current to both the expiratory and inspiratory muscles at the same time.

The method and system described herein, for the first time, describes restoration of both inspiratory muscle function to restore breathing and expiratory muscle function to restore an effective cough in the same individual. Additionally, the method and system enables the user to selectively activate the inspiratory or expiratory muscles when desired, so that the user can for example produce an effective cough when needed. The method and system is also configured to limit or prevent the flow of electrical current to both the expiratory and inspiratory muscles at the same time.

In one aspect, the method and system described herein selectively activates the expiratory muscles and allows for the opening of the glottis at the time of complete expiratory muscle contraction but before the next inspiration by diaphragm pacing so that the entire cough occurs within the 3 to 4 seconds after the inspiration. Thus, the precise timing required for a normal respiratory cycle is accomplished by the present method and system.

According to certain illustrative embodiments, the method comprises selectively activating inspiratory or expiratory muscle motor neurons in a subject having a spinal cord injury or progressive neurodegenerative disease by positioning one or more first electrical stimulators at one or more levels of the upper thoracic spinal cord of the subject and/or on or near the phrenic nerve; operating the one or more first electrical stimulators to deliver an electrical stimulation to the spinal level or levels and/or phrenic nerve; positioning one or more second electrical stimulators at one or more levels of the lower thoracic and/or upper lumbar spinal cord of the subject; and operating the one or more second electrical stimulators to deliver an electrical stimulation to the spinal level or levels. The activation of the one or more first electrical stimulators provides coordinated contraction of the inspiratory muscles to provide inspiration to restore breathing. The activation of the one or more second electrical stimulators provides coordinated contraction of the expiratory muscles to restore cough. The expiratory stimulation system may be operated periodically to deliver the electrical stimulation to the expiratory muscles resulting in the generation of an effective cough to remove airway secretions or aspirated material such as food or other foreign bodies.

According to further illustrative embodiments, the method comprises preserving function of inspiratory and expiratory motor neurons in a subject with a spinal cord injury or progressive neurodegenerative disorder comprising selectively operating (i) one or more first stimulators positioned at one or more levels of the upper thoracic spinal cord and/or on or near the phrenic nerve of the subject to deliver an electrical stimulation to the spinal cord level or levels and/or phrenic nerve to activate the inspiratory muscles and (ii) one or more second stimulators positioned at one or more levels of the lower thoracic and/or upper lumbar spinal cord of the subject to deliver an electrical stimulation to the spinal cord level or levels to activate the expiratory muscles.

Additionally provided is a system for selectively activating inspiratory or expiratory muscle motor neurons in a subject. The system comprises one or more electrical signal generators and one or more first and second stimulators electrically coupled to the one or more electrical signal generators. The one or more first stimulators being configured to be positioned at one or more levels of the upper thoracic spinal cord and/or on or near the phrenic nerve of the subject to deliver an electrical stimulation from the electrical signal generator for inspiration. The one or more second stimulators being configured to be positioned at one or more levels of the lower thoracic and/or upper lumbar spinal cord of the subject to deliver an electrical stimulation from the electrical signal generator to generate an effective cough. The one or more first and second stimulators may be electrically coupled to the same or different electrical signal generator.

BRIEF DESCRIPTION OF THE DRAWINGS

The following is a brief description of the drawings, which are presented for the purpose of illustrating certain embodiments of the system and method disclosed herein and not for the purpose of limiting the same.

DETAILED DESCRIPTION

Figure 1:
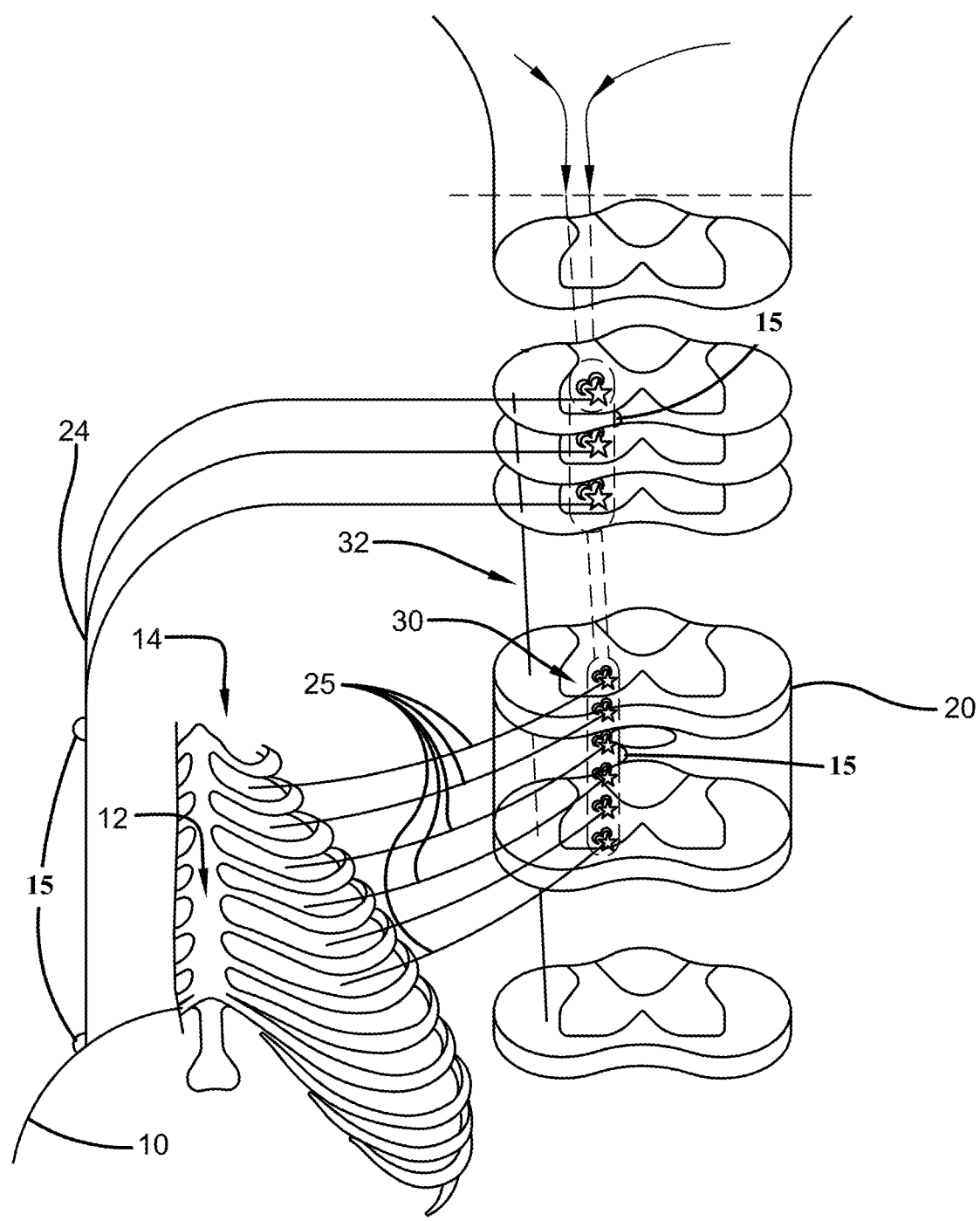
FIG. 1 is a schematic diagram of an inspiratory stimulator, such as an electrode, positioned at the upper thoracic levels of the spinal cord and the nerve pathways extending from these spinal cord levels to the diaphragm and the intercostal muscles.

A method and system are provided for selectively activating the inspiratory or expiratory muscle motor neurons in a subject to restore breathing and an effective cough respectively when desired in the same individual. The method of activating the inspiratory or expiratory muscle motor neurons in a subject includes positioning one or more first electrical stimulators on one or both phrenic nerves, in the thorax, within the muscular body of the diaphragm near the motor point of the phrenic nerve, at one or more levels of the upper thoracic spinal cord, or combinations thereof of the subject. One or more second electrical stimulators are positioned at one or more levels of the lower thoracic spinal cord, upper lumbar spinal cord, or combinations thereof of the same subject. The one or more first electrical stimulators and the one or more second electrical stimulators are selectively operated to deliver electrical stimulation to the inspiratory or expiratory muscles.

As used herein, the term "inspiratory muscles" refer to the muscles that are active during inspiration and "expiratory muscles" refer to the muscles that are active during expiration. The inspiratory muscles may include the diaphragm, the external intercostal muscles, parasternal intercostal muscles and accessory muscles. The term "muscle activation", as used herein, refers to the contraction of muscle in response to stimulation by electrical impulses.

The selective activation of the one or more first electrical stimulators effect contraction of the inspiratory muscles to restore breathing. The selective activation of the one or more second electrical stimulators effect contraction of the expiratory muscles to restore an effective cough. The method may be used to activate the inspiratory or expiratory muscle motor neurons to restore breathing in ventilator dependent subjects as well as to restore an effective cough in the same subject suffering from spinal cord injuries or from neurodegenerative disorders. The one or more first electrical stimulators and the one or more second electrical stimulators may be separately ground to limit or prevent the flow of electrical current to both the expiratory and inspiratory muscles at the same time.

In certain embodiments, the one or more first electrical stimulators are positioned at, between, or along the T1 to T6 levels of the thoracic spinal cord. In other embodiments, the one or more first electrical stimulators are positioned at the T2 level of the thoracic spinal cord. In some embodiments, the one or more first electrical stimulators are positioned at two or more levels of the upper thoracic spinal cord. At least part of the one or more first electrical stimulators may be located on or along the ventral epidural surface of the spinal cord. In some embodiments, the one or more first electrical stimulators are positioned on two or more regions of the phrenic nerve.

In certain embodiments, the one or more second electrical stimulators are positioned at, between, or along the T9 to T12 levels on the dorsal epidural surface thoracic spinal cord. In some embodiments, the one or more second electrical stimulators are positioned at, between, or along the L1 to L2 levels on the dorsal epidural surface of the spinal cord. In some embodiments, the one or more second electrical stimulators are positioned at two or more levels of the lower thoracic and/or upper lumbar spinal cord.

A system for selectively activating inspiratory or expiratory muscle motor neurons in the same subject is also provided. The system includes one or more first electrical stimulators and one or more second electrical stimulators electrically coupled to one or more electrical signal generators. The electrical signal generator selectively delivers electrical stimulation asynchronously to the inspiratory or expiratory muscle motor neurons via the first and second electrical stimulators, respectively. The electrical signal generator may be coupled to a radiofrequency transmitter. The one more first electrical stimulators are configured to be positioned at one or more levels of the upper thoracic spinal cord and/or on or near the phrenic nerve of the subject and to deliver an electrical stimulation from the electrical signal generator to the inspiratory muscles. Placing an electrode "near" the phrenic nerve means a sufficient distance from the phrenic nerve to contact it with stimulation pulses equal to or above a minimum therapeutic stimulation level.

The one more second electrical stimulators are configured to be positioned at one or more levels of the lower thoracic and/or upper lumbar spinal cord of the subject to deliver an electrical stimulation from the electrical signal generator to the expiratory muscles. The first and second electrical stimulators may be coupled to a single electrical signal generator or to separate electrical signal generators.

The one or more first and/or second electrical stimulators may comprise a unipolar, bipolar or tripolar stimulating electrode (e.g., wire lead electrodes, disc electrodes, nerve cuff electrodes, etc.) that is configured to be implanted either non-invasively through a wire, or via a laminectomy incision.

The system to activate the inspiratory muscles may deliver an electrical stimulation having a stimulus frequency of about 10 to about 20 hertz (Hz) and a pulse amplitude of about 1 to about 2 milliamps (mA) when the stimulators are applied directly to the phrenic nerve. The system to activate the inspiratory muscles may deliver an electrical stimulation having a stimulus frequency of about 15 to about 20 Hz and a pulse amplitude of about 20 to about 25 mA when implanted directly into the muscular body of the diaphragm. The system to activate the inspiratory muscles may deliver an electrical stimulation having a stimulus frequency of about 300 to about 500 Hz and a pulse amplitude of about 0.5 to about 5 mA when applied to the ventral epidural surface of the upper thoracic spinal cord.

The system to activate the expiratory muscles may deliver an electrical stimulation having a stimulus frequency of about 40 to about 500 Hz, a pulse amplitude of about 1 to 40 mA, and a voltage of about 0.5 to about 40 V.

Electrical activation of the inspiratory muscles, such as the diaphragm, may be achieved by the placement of one or more first electrical stimulators directly on one or both the phrenic nerves, in the thorax bilaterally, near the motor point of the phrenic nerve where it enters the diaphragm bilaterally, or at one or more levels of the upper thoracic spinal cord. In certain embodiments, the one or more first electrical stimulators are disc, wire or cuff electrodes. Phrenic nerve electrodes can be placed in the thorax via thoracoscopic techniques or thoracotomy, or within the diaphragm via laparoscopic techniques. This method has been shown to restore inspiratory breathing in patients with ventilator dependent respiratory failure secondary to cervical spinal cord injury. In many patients, this technique results in liberation from mechanical ventilation and the many disadvantages of this modality. The electrodes may be activated by an external electrical signal generator powered by a battery or other means known in the art.

Electrical activation of the expiratory muscles may be achieved by the placement of one or more second electrical stimulators at one or more levels of the lower thoracic spinal cord, the upper lumbar spinal cord, or combinations thereof of the subject. In certain embodiments, the one or more second electrical stimulators are disc, wire or cuff electrodes. In certain embodiments, the one or more second electrical stimulators are placed on the epidural dorsal surface of the spinal cord at the T9 and T11 spinal levels. Disc electrodes can be placed via mini-laminectomy incisions and wire electrodes can be placed using minimally invasive methods. In certain embodiments, wire electrodes may be implanted along the dorsal epidural surface of the spinal cord at the upper thoracic and/or upper portion of the lumbar spinal cord to activate the expiratory muscles to restore cough. The electrodes may be activated by an external electrical signal generator powered by a battery or other means known in the art.

In certain embodiments, placement of each electrical stimulation system (i.e., the inspiratory stimulation system and the expiratory stimulation system) includes the placement of separate ground electrodes for each system. The separate ground electrodes prevent the simultaneous activation of both the inspiratory and expiratory muscles and potential damage to one or both of the neuromuscular stimulation systems. In certain embodiments, the inspiratory electrical stimulation system includes its own ground electrode to provide a limited distribution of electrical current in the vicinity of the inspiratory muscles, such as the diaphragm. In certain embodiments, the expiratory stimulation system includes its own ground electrode to provide a limited distribution of electrical current in the vicinity of the motor roots innervating the expiratory muscles. The use of the separate ground electrodes prevents the spread of electrical current and simultaneous activation of both the inspiration and expiration muscles.

Use of inspiratory and expiratory electrical stimulation systems to restore breathing and generate an effective cough in a subject requires the coordinated electrical activation of both stimulation systems separated in time. In an orderly fashion, electrical stimulation of the inspiratory muscles, with or without a coincident maximum inspiratory effort by the patient, is used to generate a large inhalation over a 1 to 1.5 second period. Crucial to the proper activation of the selective and asynchronous activation of the inspiratory and expiratory muscles is the proper activation timing of each group of respiratory muscles. Upon cessation of the inspiratory electrical stimulation with the lungs in an inflated state, voluntary closure of the glottis or manual obstruction of the tracheostomy tube occurs. Subsequently, the expiratory muscles are temporarily activated/contracted to generate a large expiratory (positive) pressure. Activation of the expiratory muscles must occur just prior to opening of the glottis in synchrony with opening of the glottis or release of tracheal obstruction. The system and method described herein restores both sets of respiratory muscles, thereby allowing for the first time, restoration of both inspiratory and expiratory muscle function in the same patient.

The human spinal cord is divided into the cervical, thoracic, lumbar, sacral, and coccygeal levels. The cervical and upper thoracic regions provide activation signals to the thoracic diaphragm through the phrenic nerves. The thoracic region includes twelve levels, numbered T1-T12, of which T1-T6 are upper thoracic levels and T9-T12 are lower thoracic levels. The lumbar region includes five levels, numbered L1-L5, of which L1-L2 are the upper lumbar levels for purposes of this application. T1-T6 provide activation of the diaphragm through the phrenic nerve and the intercostal muscles through the intercostal nerves.

According to certain embodiments, the method of activating inspiratory muscles includes positioning one or more first electrodes at one or more levels of the upper thoracic spinal cord of a subject on the ventral epidural surface and operating the electrode to deliver electrical stimulation to the upper thoracic spinal cord level or levels. According to certain embodiments, the method of activating expiratory muscles includes positioning one or more second electrodes at one or more levels of the lower thoracic (T9-T12) and/or upper lumbar (L1-L2) spinal cord on the dorsal epidural surface of a subject and operating the one or more second electrodes to deliver electrical stimulation to the lower thoracic and/or upper lumbar spinal cord at the one or more levels.

In order to determine the most effective segment or segments for receiving spinal cord stimulation for particular individuals or species, the spinal cord and surrounding tissue can be evaluated to determine the position for electrode placement using techniques known to those skilled in the art. See for example the discussion of electrode placement in U.S. Pat. No. 5,999,855 to Anthony F. DiMarco, the disclosure of which is incorporated herein by reference.

The external controlling circuitry of the inspiratory and expiratory stimulation systems can be adjusted to provide timing parameters to selectively activate the inspiratory or expiratory muscles at the desired times. The electrical stimulation can be provided in a variety of waveforms, such as sinusoidal, stepped, or trapezoidal waveforms, and can vary in terms of amplitude, frequency, timing, and pulse width.

According to illustrative embodiments, electrical stimulation refers to frequencies greater than about 5 Hz. According to other embodiments, the one or more first and/or second electrical stimulators deliver an electrical stimulation having a frequency of about 40 Hz to about 500 Hz. In some embodiments, the one or more first and/or second electrical stimulators deliver an electrical stimulation having a frequency from about 100 to about 300 Hz.

For both inspiratory and expiratory muscle stimulation systems, the electrical stimulation can have a pulse amplitude of about 0.1 to about 50 mA. In some embodiments, the electrical stimulation has a pulse amplitude of about 0.5 to about 25 mA. In certain embodiments, the electrical stimulation has a pulse amplitude of about 0.5 mA to about 5 mA. In certain embodiments, the electrical stimulation has a pulse amplitude of about 0.5 mA to about 3 mA.

The electrical stimulation for both inspiratory and expiratory systems may be applied at a voltage of about 0.1 V to about 50 V.

In certain embodiments, the electrical stimulation of the one or more first and/or second stimulators is applied with a pulse width of about 10 microseconds to about 10 seconds. In certain embodiments, the pulse width of the inspiratory stimulation system can be varied between 0.1 and 0.5 milliseconds, optionally about 0.05 to about 0.3 milliseconds. Cycle on-time and off-time for the activation of the inspiratory muscles may be adjusted to about 0.5 to about 1.8 seconds and about 2 to about 6 seconds, respectively. Cycle on-time for the activation of the expiratory muscles may be adjusted to about 300 to about 1000 milliseconds. In certain embodiments, the pulse width of the expiratory stimulation system can be varied between about 200 to about 400 microseconds.

Pulse train rate (breaths per min) for the activation of the inspiratory muscles can be varied between about 6 to about 23 breaths/minute. In certain embodiments, the pulse train rate varies from about 7 to about 15 breaths/minute. Pulse train rate for the activation of the expiratory muscles may be established at about 2 to about 3 breaths/minute or much less frequently, as may be required to generate a cough, e.g., to remove airway secretions or aspirated material such as food or other foreign bodies.

Electrical stimulators such as electrodes for spinal cord or direct nerve stimulation can be inserted percutaneously into or onto the nerves or close to the nerves or spinal cord region. Alternatively, the stimulators can be placed via a laminectomy or hemi-laminectomy incision onto the epidural surface of the spinal cord. The one or more first electrical stimulators may be positioned on the ventral surface of the upper thoracic spinal cord and/or near or on the phrenic nerve. The one or more second electrical stimulators may be positioned on the dorsal surface of the lower thoracic or upper lumbar spinal cord. The one or more first and/or second electrical stimulators can be placed anywhere within the region near the target spinal cord segments. The one or more first and/or second electrical stimulators may be introduced into the epidural space of the spinal cord levels either by a percutaneous approach or by surgical laminectomy or laminotomy. In some embodiments, one or more first and/or second electrical stimulators that can be implanted less invasively, e.g., through a large bore needle by percutaneous means, can be used in order for implantation to be carried out in a relatively non-invasive manner.

Figure 5:
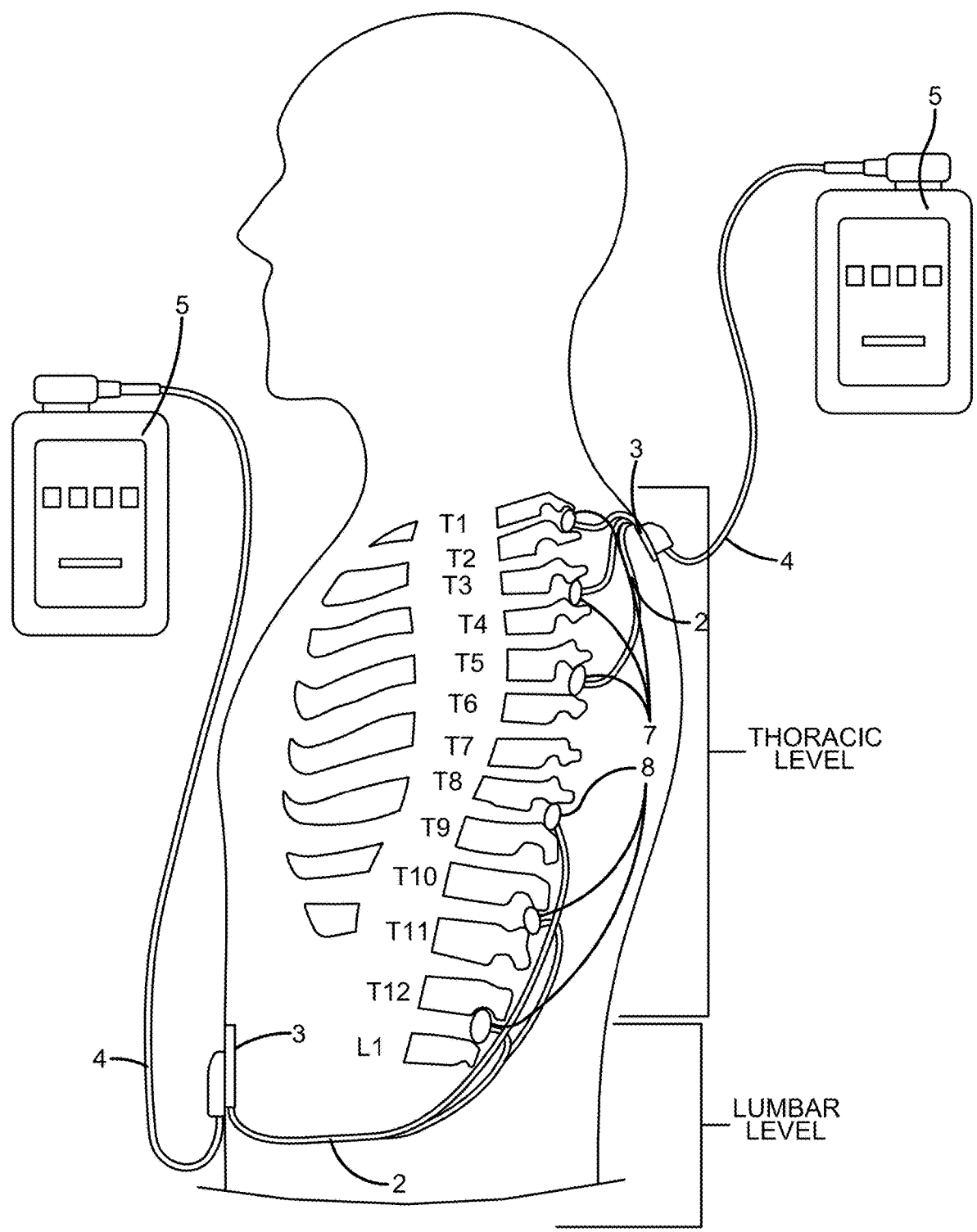
FIG. 5 is the illustration according to FIG. 4 wherein the first and second electrodes for selectively stimulating inspiratory or expiratory function are electrically coupled to different electrical signal generators.

A variety of electrodes are suitable for providing electrical stimulation to the phrenic nerve and/or to segments of the spinal cord. For example, commercially available disc spinal cord electrodes (e.g., Medtronic #3586; 4 millimeter) can be used (FIG. 5). In certain embodiments a tripolar stimulating electrode can be used.

The method of selectively activating the inspiratory muscles by electrical stimulation can generate the inspiratory volume in a subject suffering from respiratory failure. For example, it can result in an inspired volume of up to about 80% of the inspiratory capacity. The actual lung volume varies among subjects. The total lung capacity for an adult human, which is the volume of gas contained in the lung at the end of maximal inspiration, is typically about 6 liters. Importantly, this method of stimulation can provide ventilation for prolonged periods of time, such as from 18 hours a day up to 24 hours a day.

An electrical signal generator governs the signal delivered by the one or more first and/or second electrical stimulators. Depending on its size, the electrical signal generator can be placed together with the one or more first and/or second electrical stimulators, or it may simply be in communication with the one or more first and/or second electrical stimulators. A variety of suitable electrical signal generators are available. Non-limiting examples include a modified Finetech electrical stimulator, with parameter ranges of 0-40 volts, 10-600 Hz, and 0.1-1 millisecond pulse width.

In certain embodiments, the system can include a stimulation apparatus that can include an electrical signal generator (similar to the one described above) and a breathing sensor and control circuit that is in electrical communication with the electrical signal generator and the flow sensor. The breathing sensor and control circuit can be configured to detect certain breathing attributes of the subject (e.g., the inspiration phase of a breath, the duration of the inspiration phase, the exhalation phase of a breath, the duration of the exhalation phase, tidal volume, and/or flow rate), convert these attributes to signals, and communicate these signals to the electrical signal generator. The electrical signal generator then sends a signal to the one or more first and/or second electrical stimulators.

In certain embodiments, the system may be used to activate the expiratory muscles to restore cough in subjects who currently have an implanted electrical device to activate the diaphragm to restore breathing. In certain embodiments, the system may be used to activate the diaphragm to restore breathing in subjects who currently have an implanted electrical device to activate the expiratory muscles to restore cough.

In some embodiments, electrical stimulation of the inspiratory muscles can be synchronized with attempts at breathing or breathing made by the subject (e.g., on the subject's own or by the mechanical ventilator). For example, electrical stimulation can be triggered following the inspiration phase of the breath (i.e., during exhalation) to maximize the contraction during the period when the diaphragm is at its longest length.

Another aspect of the method and system provides a means for treating respiratory dysfunction or failure in a subject that includes selectively operating the one or more first electrical stimulators and the one or more second electrical stimulators to deliver the respective electrical pulses to the inspiratory or expiratory muscles. Respiratory dysfunction or failure can be treated entirely through electrical stimulation, or it can also include the step of delivering breathing gas from a ventilator to the subject, at least a portion of which is inhaled upon activation of the diaphragm and intercostal muscles.

Respiratory dysfunction or failure that can be treated by the method and system described herein can occur as a result of a variety of conditions, such as amyotrophic lateral sclerosis, muscular dystrophy, stroke, drug overdose, brain injury, or spinal cord injury. The method and system can also be used to treat subjects that have suffered a partial or complete loss of phrenic nerve function. While loss of phrenic nerve function can decrease the response of the diaphragm to electrical stimulation, the method and system still provides electrical stimulation to the other inspiratory muscles and therefore can continue to provide treatment for such subjects.

The presently disclosed method and system is readily understood when read in conjunction with illustrative FIGS. 1 to 8. It should be noted that the method and system is not limited to any of the embodiments shown in the drawing figures, but rather should be construed in breadth and scope in accordance with the disclosure provided herein.

FIG. 1 is an illustration of a human patient who has been implanted with electrodes 15 positioned at the thoracic 20 levels of the spinal cord, the nerve pathways 25 extending from these spinal cord levels to the diaphragm 10 and/or the external intercostal muscles 12, and the within the muscular body of the diaphragm near the motor point of the phrenic nerve. The diaphragm 10 is a sheet of muscle extending across the lower portion of the ribcage 14. When the diaphragm 10 contracts, it substantially shortens, increasing the volume of the thorax, expanding the lungs and creating a pressure differential that draws air into the lungs. The intercostal muscles 12 are located between the ribs and help form and move the chest wall. Activation of the external intercostal muscles 12 aids in the process of expanding the lungs by lifting and separating the ribs during inhalation. If the inspiratory muscles are weak or paralyzed, the lungs may not fully expand with each breath. With the electrodes positioned on or near the vicinity of the phrenic nerve 24, restoration of diaphragm function can be achieved. With electrodes 15 positioned on the ventral surface of the upper thoracic spinal cord 20, restoration of both the diaphragm 10 and inspiratory intercostal muscles 12 can be achieved. Stimulation of the upper thoracic region 20 of the spinal cord can result in signals being sent to the intercostal motor neuron pools 30 resulting in activation of the intercostal nerves 25. The ascending pathways mediating the intercostal to phrenic reflex effects are located bilaterally in the ventrolateral funiculi 32.

Figure 2:
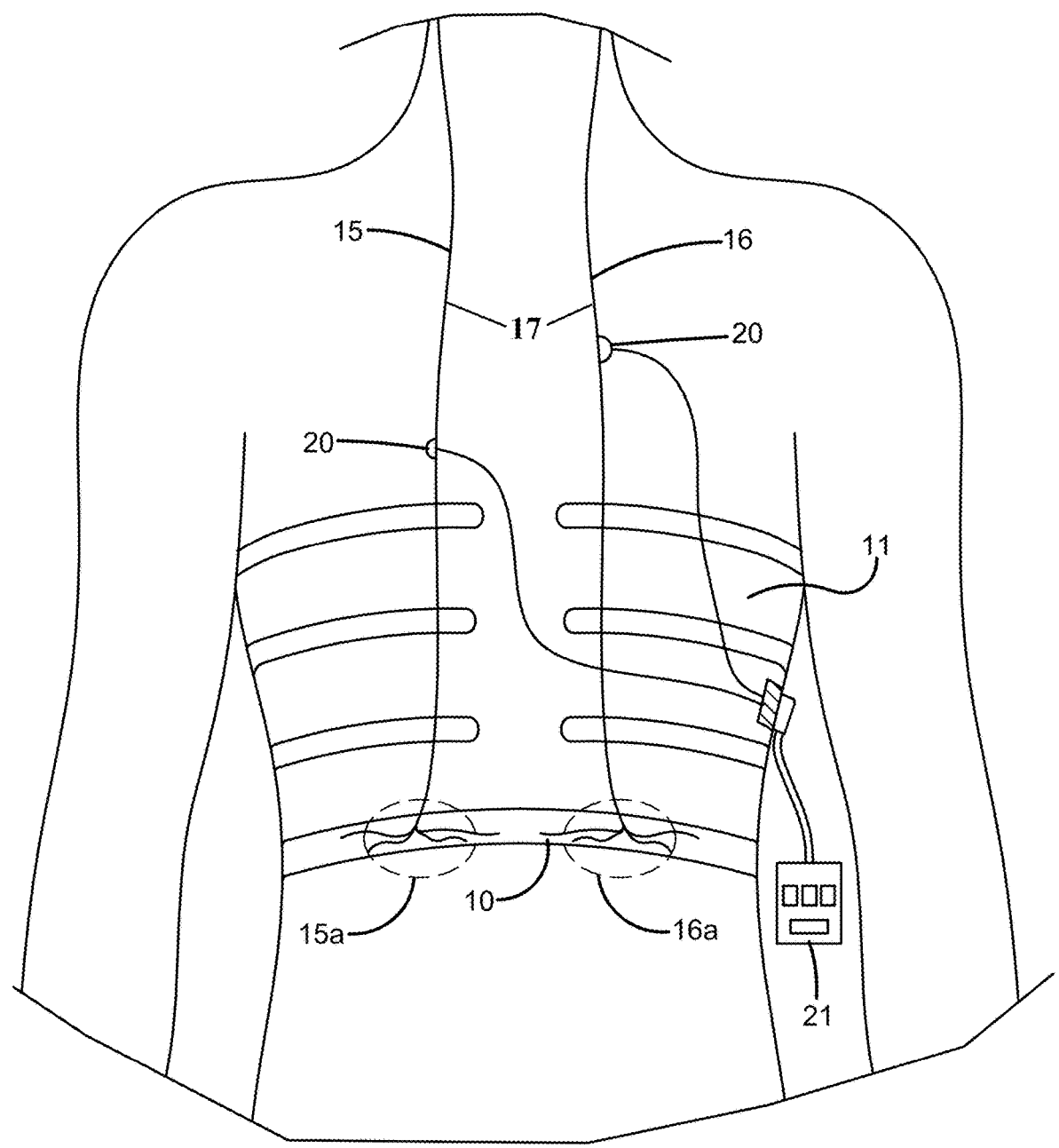
FIG. 2 is an illustration of a human patient who has been implanted with electrodes on the right and left branches of the phrenic nerve in the thorax, wherein the phrenic nerve forms sub-branches in the tissue associated with the diaphragm.

FIG. 2 is an illustration of a human patient who has been implanted with electrodes 20 on the right 15 and left 16 branches of the phrenic nerve 17 in the thorax 11, wherein the phrenic nerve 17 forms sub-branches 15a and 15b in the tissue associated with the diaphragm 10. Electrodes 20 are electrically coupled to an electrical signal generator 21 that delivers a stimulating pulse to the phrenic nerve 17 to restore inspiratory muscle function.

Figure 3:
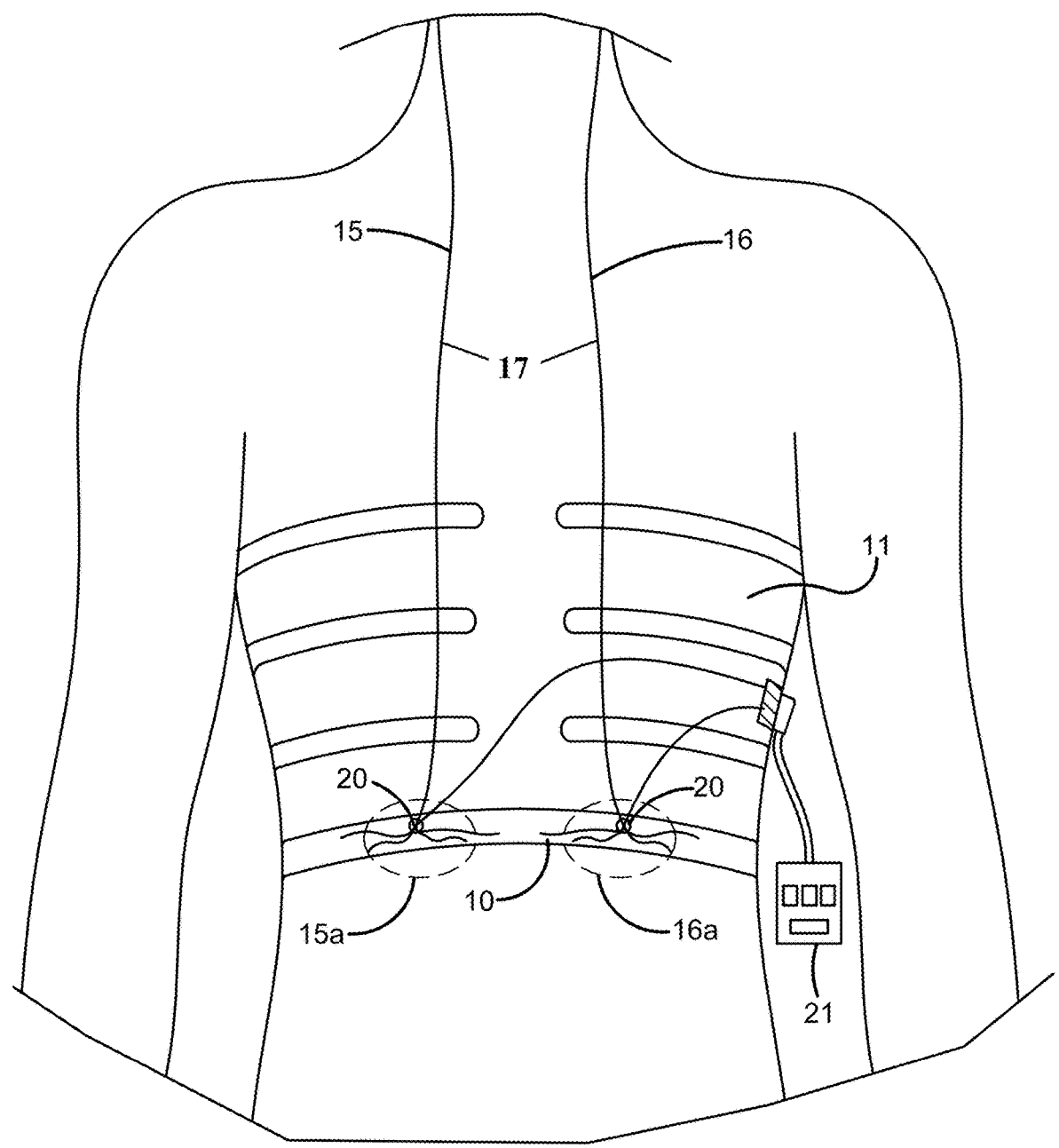
FIG. 3 is an illustration of a human patient who has been implanted with electrodes within the muscular portion of the diaphragm near the phrenic nerve motor points to activate the diaphragm to restore inspiratory muscle function.

FIG. 3 is an illustration of a human patient who has been implanted with electrodes 20 within the muscular portion of the diaphragm 10 near the phrenic nerve 17 motor points 15a and 15b to activate the diaphragm 10 to restore inspiratory muscle function. Electrodes 20 are electrically coupled to an electrical signal generator 21 that delivers a stimulating pulse near the phrenic nerve 17 motor points 15a and 15b within the muscular portion of the diaphragm 10.

Figure 4:
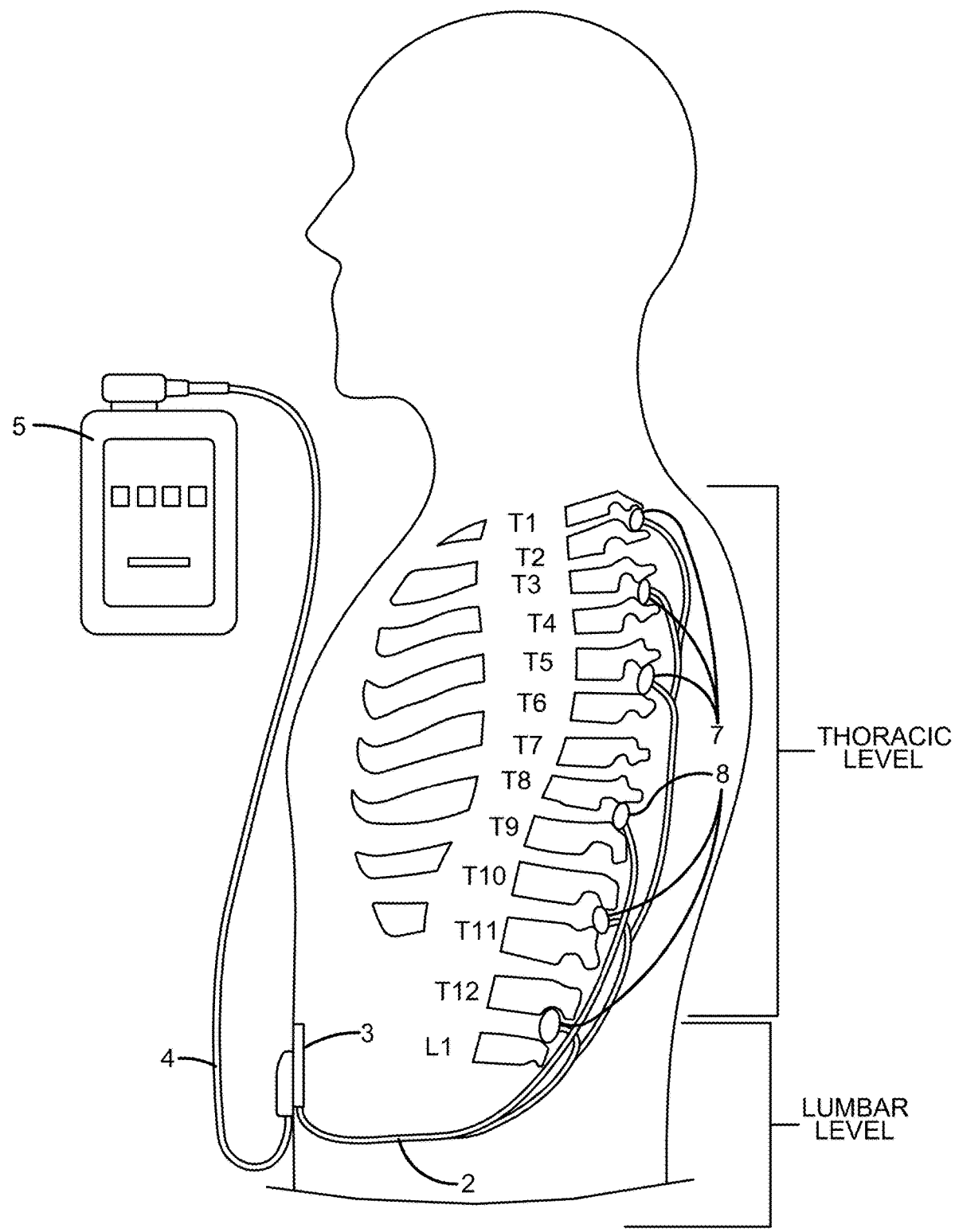
FIG. 4 is an illustration of a human patient who has been implanted with first electrodes at the upper thoracic levels of the spinal cord to selectively stimulate inspiratory function and second electrodes at the lower thoracic and upper lumbar levels of the spinal cord to selectively stimulate expiratory function, wherein the first and second electrodes are electrically coupled to one electrical signal generator.

FIG. 4 is an illustration of a human patient who has been implanted with first electrodes 7 at the upper thoracic levels of the spinal cord to stimulate inspiratory function and second electrodes 8 at the lower thoracic and upper lumbar levels of the spinal cord to stimulate expiratory function, wherein the first 7 and second 8 electrodes are electrically coupled to one portable external electrical signal generator 5. A radiofrequency receiver 3 is positioned in a subcutaneous pocket over the anterior chest wall. Electrical wires 2 connect the electrodes 7 and 8 to the receiver 3. Stimulation is applied via an external antenna 4 by activating the electrical signal generator 5 to each electrode 7 and 8 alone and in combination.

FIG. 5 is an illustration of a human patient who has been implanted with first electrodes 7 at the upper thoracic levels of the spinal cord to stimulate inspiratory function and second electrodes 8 at the lower thoracic and upper lumbar levels of the spinal cord to stimulate expiratory function, wherein the first 7 and second 8 electrodes are electrically coupled to different portable external electrical signal generator 5. A radiofrequency receiver 3 is positioned in a subcutaneous pocket over the anterior chest wall. Electrical wires 2 connect the electrodes 7 and 8 to the receiver 3. Stimulation is applied via an external antenna 4 by activating the external electrical signal generator 5 to each electrode alone and in combination.

Figure 6:
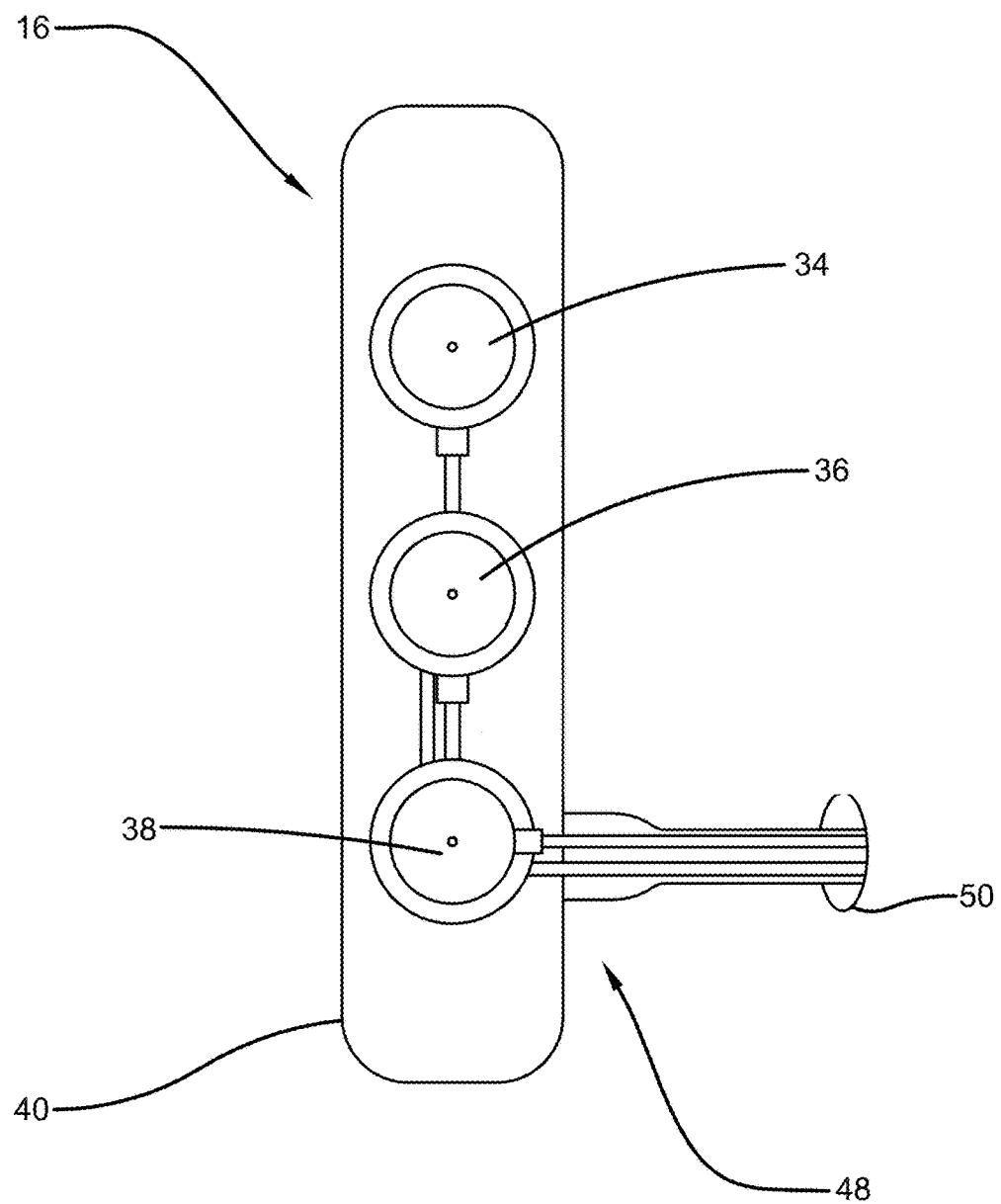
FIG. 6 is a schematic of an electrode that may be positioned surgically via a laminectomy using electrodes near a spinal segment in order to electrically stimulate the spinal cord and the inspiratory and expiratory motor neuron pools located therein.

FIG. 6 is a schematic of an electrode 16 that may be positioned surgically via a laminectomy using electrodes near a spinal segment in order to electrically stimulate the spinal cord and the inspiratory and expiratory motor neuron pools located therein. Three electrode plates 34, 36 and 38 are disposed in a silicon rubber insulating body portion 40. Each of the electrode plates 34, 36 and 38 are made from a platinum/iridium or pure platinum composition and are collinearly spaced apart on the body 40. A spacing distance of about 9 mm between each electrode plate center can be used. In order to establish an optimal stimulation transfer, each of the electrode plates 34, 36 and 38 are of uniform size and construction. The cross-sectional diameters of each of the electrode plates may be 4.5 mm. The overall length and width of the insulating silicon rubber body 40 may be 35 mm and 7.5 mm respectively, although any suitable length and width may be determined by one having ordinary skill in the art. The electrode 16 can be placed onto the ventral or dorsal surface of the spinal cord of a subject via a laminectomy incision. Connecting wires are attached to the leads forming the bundle 50 that forms an extension for connection to a demodulator circuit. The anode of the spinal cord electrode is preferably located several centimeters distal to the cathode located on the surface of the spinal cord. In that orientation a broad electric field is generated. The broad electric field induces electrical activity in the spinal cord effecting inspiratory muscle stimulation. The center of the electrode is positioned in the midline over this region of the spinal cord. The electrode can be positioned in the midline under fluoroscopic guidance to provide inspiratory muscle activation.

Figure 7:
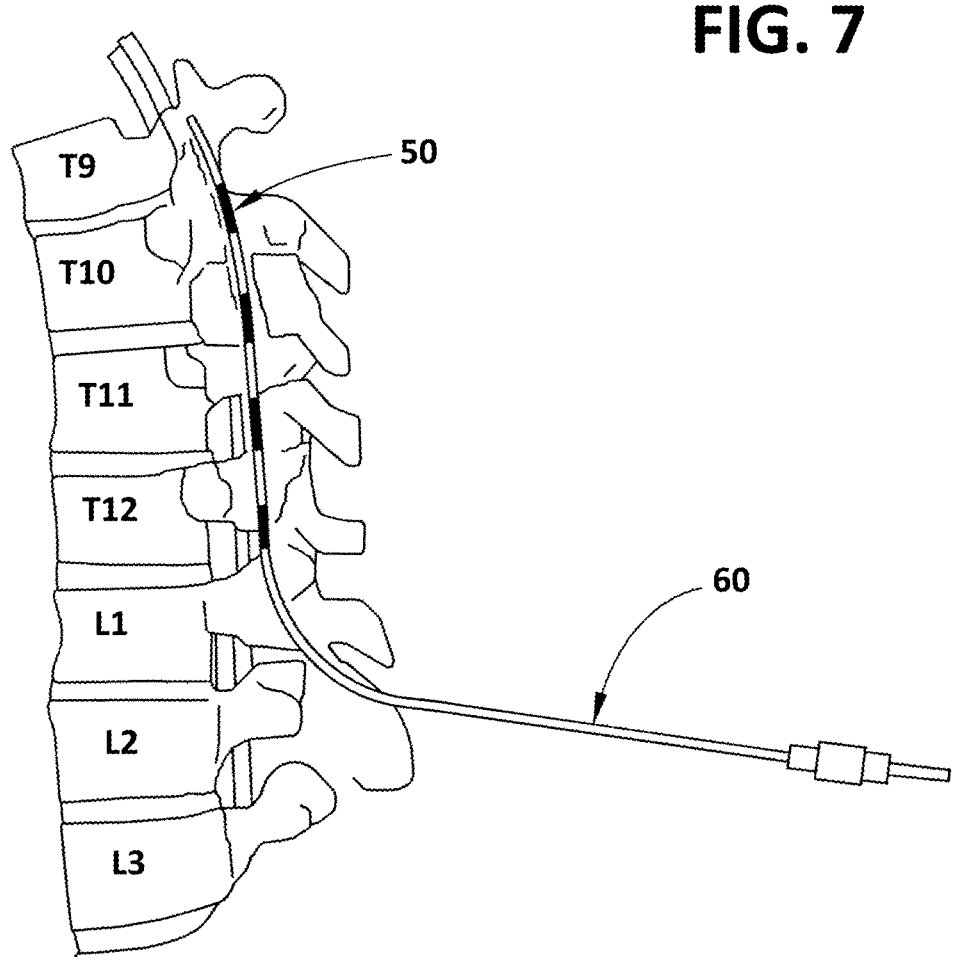
FIG. 7 is an illustration showing wire electrodes implanted along the dorsal epidural surface of the spinal cord at the lower thoracic and upper lumbar spinal cord levels to activate the expiratory muscles to restore cough.
Figure 8:
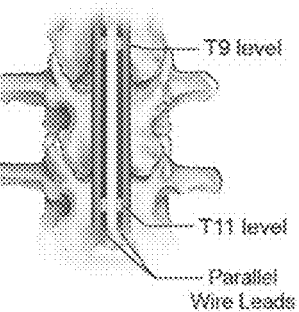
FIG. 8 is an illustration of a human patient who has been implanted with electrodes on the right and left branches of the phrenic nerve, wherein the phrenic nerve forms sub-branches in the tissue associated with the diaphragm; also depicted are parallel wire leads positioned along the T9 to T12 levels on the dorsal epidural surface of the thoracic spinal cord.
Figure 8:
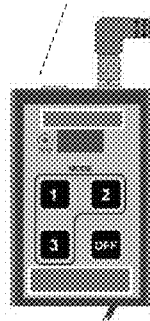
Figure 8:

FIG. 7 is an illustration showing wire electrodes 50 implanted along the dorsal epidural surface of the spinal cord at the upper thoracic and upper portion of the lumbar spinal cord to activate the expiratory muscles to restore cough. This can be achieved using minimally invasive techniques, for example using an insertion needle 60 through an incision of 1 to 1.5 cm in size.

While the system and method for selectively activating inspiratory or expiratory muscles by electrical stimulation has been described above in connection with certain illustrative embodiments, it is to be understood that other embodiments may be used or modifications and additions may be made to the described embodiments for performing the same function without deviating therefrom. Furthermore, all embodiments disclosed are not necessarily in the alternative, as various embodiments may be combined to provide the desired characteristics. Variations can be made by one having ordinary skill in the art without departing from the spirit and scope hereof. Therefore, the system and method should not be limited to any single embodiment, but rather construed in breadth and scope in accordance with the recitation of the attached claims.

The invention claimed is:

1. A method for producing coordinated contraction of inspiratory muscles to restore breathing and coordinated contraction of expiratory muscles to restore cough in a subject comprising:

positioning one or more first electrical stimulators at any one of the following: (i) directly on one or both phrenic nerves in the cervical region, (ii) in the thorax, (iii) within the muscular body of the diaphragm near the motor point of the phrenic nerve, (iv) at one or more levels of the upper thoracic spinal cord, or (v) combinations thereof of the subject;

activating the inspiratory muscles by operating the one or more first electrical stimulators to deliver an electrical stimulation directly to the upper thoracic spinal cord and/or the phrenic nerve;

positioning one or more second electrical stimulators at one or more levels of the lower thoracic spinal cord, upper lumbar spinal cord or combinations thereof of the subject;

activating the expiratory muscles by operating the one or more second electrical stimulators to deliver an electrical stimulation directly to the lower thoracic spinal cord and/or upper lumbar spinal cord;

wherein the one or more first and second stimulators are electrically connected to one or more electrical signal generators;

wherein the one or more first and second stimulators selectively deliver an electrical stimulation to inspiratory and expiratory muscle motor neurons of the subject, wherein the electrical stimulation delivered by the first and second electrical stimulators generates an asynchronous electromyogram signal in the inspiratory and expiratory muscles; and separately grounding the one or more first electrical stimulators and one or more second electrical stimulators to limit or prevent the flow of electrical current to both the expiratory and inspiratory muscles at the same time.

2. The method of claim 1, wherein the one or more first and second stimulators comprise disc, wire or cuff electrodes.

3. The method of claim 1, wherein the one or more first stimulators and the one or more second stimulators are electrically connected to a single electrical signal generator.

4. The method of claim 1, wherein the one or more first stimulators and the one or more second stimulators are electrically connected to separate electrical signal generators.

5. The method of claim 1, wherein activation of the inspiratory and expiratory muscle motor neurons comprises applying unipolar stimulation.

6. The method of claim 1, wherein activation of the inspiratory and expiratory muscle motor neurons comprises applying multipolar stimulation.

7. The method of claim 1, wherein activating the inspiratory muscles comprises activating the diaphragm, the external intercostal muscles, parasternal intercostal muscles, accessory muscles, or combinations thereof.

8. The method of claim 7, wherein activating the inspiratory muscles comprises activating the diaphragm and the external intercostal muscles.

9. The method of claim 1, comprising positioning the one or more first stimulators at or between the T1 to T6 levels of the thoracic spinal cord.

10. The method of claim 9, comprising positioning the one or more first stimulators at the T2 level of the thoracic spinal cord via laminotomy incision.

11. The method of claim 1, comprising positioning the one or more first stimulators at two levels of the upper thoracic spinal cord.

12. The method of claim 1, wherein at least part of the one or more first stimulators is located on a ventral epidural surface of the spinal cord.

13. The method of claim 1, further comprising positioning the one or more first stimulators on the phrenic nerve.

14. The method of claim 1, further comprising positioning the one or more first stimulators near a motor point of the phrenic nerve where it enters the diaphragm.

15. The method of claim 1, comprising positioning the second stimulators on a dorsal epidural surface of the spinal cord at more than one level of the lower thoracic spinal cord and/or the upper lumbar spinal cord.

16. The method of claim 1, wherein at least part of the one or more second stimulators is located on a dorsal epidural surface of the spinal cord.

17. The method of claim 1, comprising positioning the one or more second stimulators at or between the T9 to T12 levels on a dorsal epidural surface of the thoracic spinal cord.

18. The method of claim 1, comprising positioning the one or more second stimulators at or between the L1 to L2 levels on a dorsal epidural surface of the lumbar spinal cord.

19. The method of claim 1, wherein the one or more first and/or second stimulators deliver an electrical stimulation having a frequency of about 10 Hz or greater.

20. The method of claim 1, wherein the electrical stimulation of the one or more first or second stimulators has a pulse amplitude from about 0.1 milliamps to about 50 milliamps.

21. The method of claim 1, wherein the electrical stimulation of the one or more first or second stimulators is applied at a voltage of about 0.1 V to about 50 V.

22. The method of claim 1, wherein the electrical stimulation of the one or more first or second stimulators is applied with a pulse width of about 10 microseconds to about 10 seconds.

23. The method of claim 1, wherein a cycle on-time and a cycle off-time for activating the inspiratory muscles is adjusted to about 0.5 to about 1.8 seconds and about 2 to about 6 seconds, respectively.

24. The method of claim 1, wherein a cycle on-time for activating the expiratory muscles is adjusted to about 300 to about 1000 milliseconds.

25. The method of claim 1, wherein a pulse train rate for activating the inspiratory muscles is from about 6 to about 23 breaths/minute.

26. The method of claim 1, wherein a pulse train rate for activating the expiratory muscles is from about 2 to about 3 times/minute.

27. The method of claim 1, comprising generating an asynchronous electromyogram signal by coordinated electrical stimulation of the inspiratory or expiratory muscles.

28. A method of restoring function of inspiratory and expiratory motor neurons and inspiratory and expiratory muscle function in a subject comprising:
   generating an electrical stimulation with an electrical generator electrically coupled to one or more first electrical stimulators and one or more second electrical stimulators;
   selectively operating one or more first stimulators to deliver an electrical stimulation directly to the phrenic nerve and/or to one or more levels of the upper thoracic spinal cord, and one or more second stimulators to deliver an electrical stimulation directly to the lower thoracic and/or upper lumbar spinal cord of the subject, to produce coordinated contraction of inspiratory muscles and expiratory muscles in the subject, wherein the electrical stimulation by the first and second electrical stimulators generates an asynchronous electromyogram signal in the inspiratory and expiratory muscles; and
   separately grounding the one or more first electrical stimulators and one or more second electrical stimulators to limit or prevent the flow of electrical current to both expiratory and inspiratory muscles at the same time.

29. A system for selectively activating inspiratory or expiratory muscles in a subject comprising:
   one or more electrical signal generators electrically coupled to one or more first electrical stimulators and one or more second electrical stimulators; the one or more first stimulators are configured to be positioned on the phrenic nerve and/or at one or more levels of the upper thoracic spinal cord of the subject; the one or more second stimulators are configured to be positioned at one or more levels of the lower thoracic and/or upper lumbar spinal cord, wherein said one or more first electrical stimulators and one or more second electrical stimulators selectively deliver electrical stimulation from the one or more electrical signal generators,
   a ground electrode for the one or more first electrical stimulators; and
   a ground electrode for the one or more second electrical stimulators;
   wherein the one or more first electrical stimulators and one or more second electrical stimulators are separately ground to limit or prevent the flow of electrical current to both the expiratory and inspiratory muscles at the same time.

30. The system of claim 29, wherein the one or more first electrical stimulators and one or more second electrical stimulators are electrically coupled to one electrical signal generator.

31. The system of claim 29, wherein the one or more first electrical stimulators and one or more second electrical stimulators are coupled to separate electrical signal generators.

* * * * *